(12) United States Patent
Wojciechowski et al.

(10) Patent No.: US 12,636,200 B2
(45) Date of Patent: May 26, 2026

(54) NEGATIVE PRESSURE WOUND THERAPY DEVICE WITH OXYGEN CONTROL

(71) Applicant: Aatru Medical, LLC, Cleveland, OH (US)

(72) Inventors: Timothy Wojciechowski, Westlake, OH (US); Thomas E. Lash, Chardon, OH (US); John Buan, Maple Grove, MN (US); Richard L. Middaugh, Rocky River, OH (US); Edward Armstrong, Chagrin Falls, OH (US)

(73) Assignee: AATRU MEDICAL, LLC, Cleveland, OH (US)

( * ) Notice: Subject to any disclaimer, the term of this patent is extended or adjusted under 35 U.S.C. 154(b) by 216 days.

(21) Appl. No.: 18/008,714

(22) PCT Filed: Jun. 14, 2021

(86) PCT No.: PCT/US2021/037178
§ 371 (c)(1),
(2) Date: Dec. 7, 2022

(87) PCT Pub. No.: WO2021/257427
PCT Pub. Date: Dec. 23, 2021

(65) Prior Publication Data
US 2023/0218444 A1 Jul. 13, 2023

Related U.S. Application Data

(60) Provisional application No. 63/039,702, filed on Jun. 16, 2020.

(51) Int. Cl.
*A61F 13/05* (2024.01)
*A61M 1/00* (2006.01)

(52) U.S. Cl.
CPC ............... *A61F 13/05* (2024.01); *A61M 1/94* (2021.05)

(58) Field of Classification Search
CPC ......... A61F 13/05; A61M 1/94; A61M 1/962; A61M 35/30; A61M 2202/0208; A61M 1/80; A61H 9/0057; A61H 2201/105
See application file for complete search history.

(56) References Cited

U.S. PATENT DOCUMENTS

| | | | | | |
|---|---|---|---|---|---|
| 3,183,713 A | * | 5/1965 | Gilmont | .................... | G01F 1/22 |
| | | | | | 73/861.55 |
| 4,004,590 A | * | 1/1977 | Muriot | .................. | A61M 1/743 |
| | | | | | 604/326 |

(Continued)

FOREIGN PATENT DOCUMENTS

| | | |
|---|---|---|
| DE | 202013000711 | 3/2013 |
| JP | 2018535805 A | 12/2018 |

(Continued)

OTHER PUBLICATIONS

Supplementary European Search Report for European Patent Application No. 21 826 812.6 dated May 24, 2024, 8 pages.

(Continued)

*Primary Examiner* — Andrew J Mensh
*Assistant Examiner* — Eric Rassavong
(74) *Attorney, Agent, or Firm* — Rankin, Hill & Clark LLP

(57) ABSTRACT

A system for negative pressure and hypoxic tissue therapy including a chemical pump assembly, a dressing to cover a tissue site, a plurality of hoses, and a cover layer to cover a portion of the dressing. Each hose is configured to fluidly connect the dressing to the assembly. Oxygen flows from the dressing to a reactor in the assembly where the oxygen is consumed by the reactor. The hoses have different cross-sectional areas and selectable lengths, and these can be (Continued)

selected to provide a desired amount of oxygen around the tissue site. The cover layer has less permeability to air that does the dressing, nd can be used to cover a portion of the dressing to inhibit the permeation of air through the dressing and thus provide the desired amount of oxygen around the tissue site.

14 Claims, 10 Drawing Sheets

(56)  References Cited

U.S. PATENT DOCUMENTS

| | | | | |
|---|---|---|---|---|
| 4,584,997 | A * | 4/1986 | Delong | A61M 16/10 |
| | | | | 128/207.18 |
| 9,078,964 | B2 * | 7/2015 | Schuman, Jr. | A61M 39/10 |
| 9,480,830 | B1 * | 11/2016 | Azocar | A61M 1/917 |
| 10,300,180 | B1 * | 5/2019 | Quisenberry | A61N 5/0624 |
| 10,828,202 | B1 * | 11/2020 | Buan | A61M 1/962 |
| 10,881,553 | B1 * | 1/2021 | Buan | A61M 1/73 |
| 11,504,268 | B2 * | 11/2022 | Scalzo | A61F 13/00063 |
| 2001/0035185 | A1 * | 11/2001 | Christopher | A61M 16/0683 |
| | | | | 128/200.24 |
| 2008/0135044 | A1 * | 6/2008 | Freitag | A61M 16/16 |
| | | | | 128/205.24 |
| 2010/0324510 | A1 * | 12/2010 | Andresen | A61F 13/05 |
| | | | | 604/319 |
| 2011/0034861 | A1 * | 2/2011 | Schaefer | A61M 1/94 |
| | | | | 604/23 |
| 2011/0060204 | A1 | 3/2011 | Weston | |
| 2012/0013632 | A1 | 1/2012 | Yamamoto | |
| 2012/0136326 | A1 | 5/2012 | Croizat et al. | |
| 2013/0096516 | A1 * | 4/2013 | Schaefer | A61M 35/00 |
| | | | | 604/290 |
| 2014/0316330 | A1 * | 10/2014 | Fudem | A61F 13/05 |
| | | | | 604/23 |
| 2016/0067104 | A1 * | 3/2016 | Sarangapani | A61M 1/85 |
| | | | | 604/290 |
| 2016/0166781 | A1 * | 6/2016 | Sarangapani | A61M 1/98 |
| | | | | 604/23 |
| 2017/0119940 | A1 * | 5/2017 | Quisenberry | A61M 1/964 |
| 2018/0078686 | A1 * | 3/2018 | Proctor, Jr. | A61M 1/86 |
| 2018/0272096 | A1 | 9/2018 | Rubin | |
| 2018/0318137 | A1 | 11/2018 | Donda | |
| 2019/0091382 | A1 | 3/2019 | Middaugh et al. | |
| 2019/0091385 | A1 * | 3/2019 | Blott | A61M 35/30 |
| 2019/0125945 | A1 * | 5/2019 | Long | B01D 53/04 |
| 2019/0328982 | A1 * | 10/2019 | Sarangapani | A61M 1/90 |
| 2020/0289727 | A1 * | 9/2020 | Locke | A61M 39/08 |
| 2020/0316273 | A1 * | 10/2020 | Hegg | A61F 13/05 |
| 2021/0162107 | A1 * | 6/2021 | Kharkar | A61M 1/964 |
| 2022/0339343 | A1 * | 10/2022 | Long | A61M 1/96 |

FOREIGN PATENT DOCUMENTS

| | | | | |
|---|---|---|---|---|
| JP | | 2020512868 A | 4/2020 | |
| WO | WO-2013156779 A1 * | 10/2013 | | A61F 13/00042 |
| WO | WO-2017075381 A1 * | 5/2017 | | A61M 35/30 |
| WO | | 2020046410 A1 | 3/2020 | |
| WO | | 2020046907 | 3/2020 | |
| WO | WO-2020046907 A1 * | 3/2020 | | A61B 46/40 |

OTHER PUBLICATIONS

International Search Report filed in PCT/US2021/037178 mailed Sep. 17, 2021.

* cited by examiner

FIG. 1

NEGATIVE PRESSURE WOUND THERAPY DEVICE WITH OXYGEN CONTROL

BACKGROUND

Negative pressure therapy is a therapeutic treatment that utilizes negative pressure for skin treatments and restorative purposes. Negative pressure is a term used to describe a pressure that is below normal atmospheric pressure. Negative pressure therapy is utilized for several sites on the skin, such as a wound or an incision. Furthermore, negative pressure therapy is useful to manage wounds with complex healing concerns. Additionally, negative pressure therapy could also be used for cosmetic purposes like removing wrinkles.

Generally, negative pressure therapy is achieved by maintaining a reduced pressure beneath a dressing on a dressing site. A vacuum generation source, such as a pump, applies reduced pressure to the inside of the dressing on the dressing site.

SUMMARY

A system for controlling an amount oxygen in an enclosed volume includes a dressing configured to seal to tissue so as to define the enclosed volume between the dressing and the tissue; a housing defining an inner chamber, and including a reactor located in the inner chamber, the reactor being configured to chemically react with oxygen in the inner chamber; and a fluid passage connecting the inner chamber and the enclosed volume allowing for a flow of oxygen between the inner chamber and the enclosed volume. The system is configured to control the amount of oxygen in the enclosed volume by a user selecting a length of the fluid passage, selecting a cross-sectional area of the fluid passage, selecting an oxygen permeability of the dressing, combinations thereof.

A means for controlling an amount of oxygen in an enclosed volume includes at least one of: a first hose, a plurality of hoses, a second hose and a clamp, and a cover layer. The enclosed volume is defined by a dressing sealed to tissue. A fluid passage connects the enclosed volume to an inner chamber of a housing. A reactor is located in the inner chamber and is configured to chemically react with oxygen in the inner chamber. The first hose at least partially defines the fluid passage, and is configured to be selectively modified from an original length to a modified length that is less than the original length to thereby control the amount of oxygen in the enclosed volume. The plurality of hoses have different cross-sectional areas. Each of the plurality of hoses is configured to be selectively connected to the housing and to the dressing to thereby at least partially define the fluid passage and thus control the amount of oxygen in the enclosed volume. The second hose at least partially defines the fluid passage. The clamp is configured to selectively modify a cross-sectional area of the second hose and thereby control the amount of oxygen in the enclosed volume. The cover layer has a permeability to air less than the dressing and is configured to cover at least a portion of the dressing to thereby control the amount of oxygen in the enclosed volume.

BRIEF DESCRIPTION OF THE DRAWINGS

FIG. 1 is a perspective view of a chemical pump assembly.

DETAILED DESCRIPTION

Figure 1:
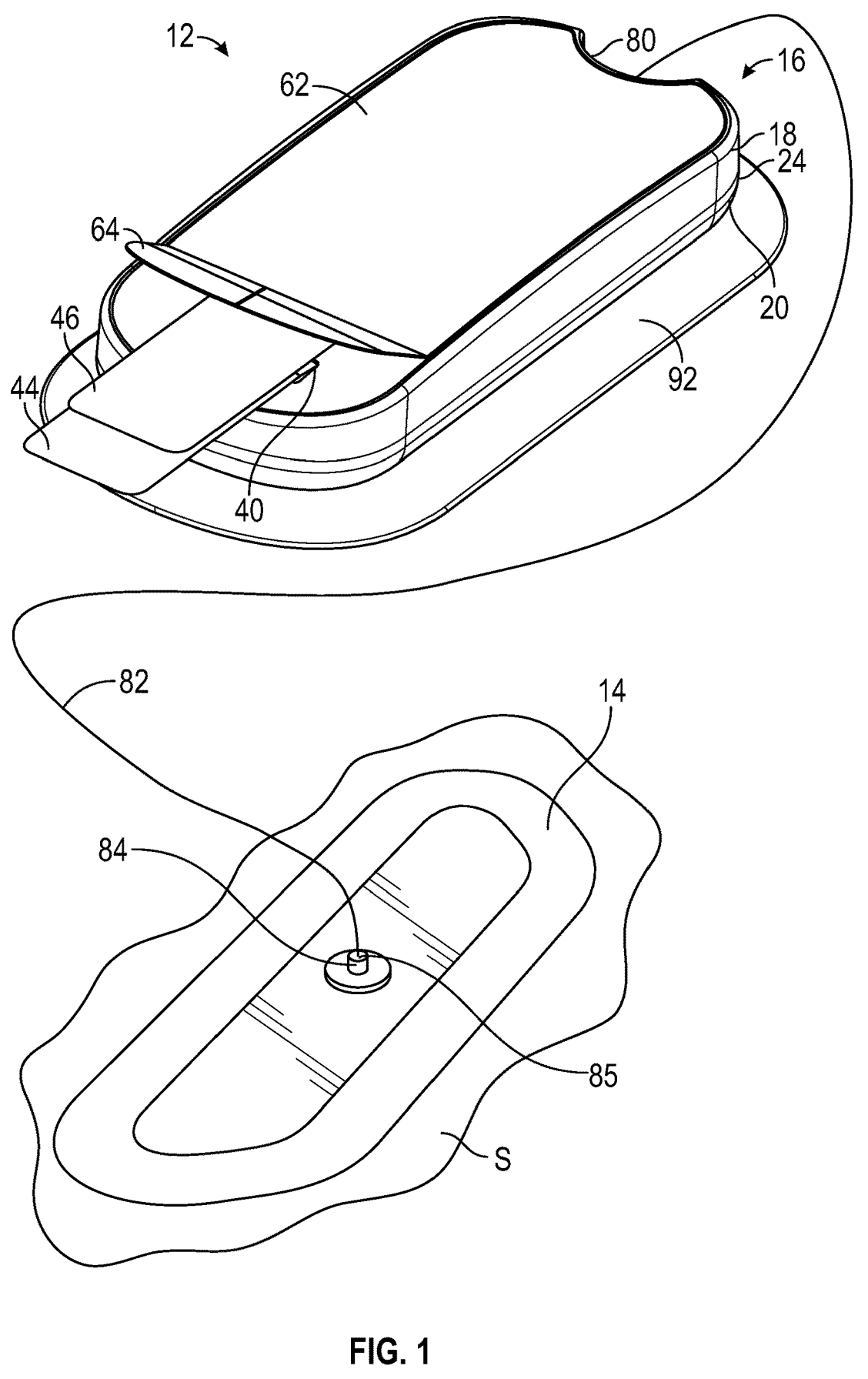
Figure 2:
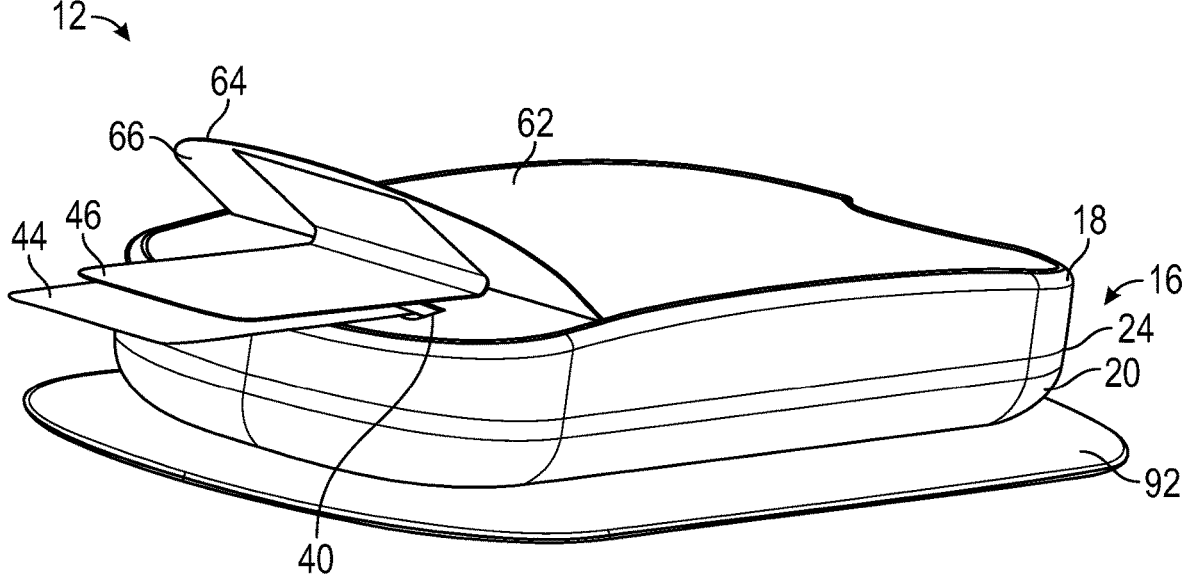
FIG. 2 is another perspective view of the chemical pump assembly.

FIG. 1 depicts a chemical pump assembly 12 system, or means that is useful for negative pressure therapy. Negative pressure described herein is pressure below atmospheric pressure. The chemical pump assembly 12 is configured to connect with a dressing 14 affixed to skin S so as to be in fluid communication with an enclosed volume beneath the dressing 14. An example of the dressing 14 that can be used with the chemical pump assembly 12 is described in U.S. application Ser. No. 16/114,813.

The chemical pump assembly 12 generally includes a chemical pump housing 16 including an upper housing 18 and a lower housing 20 that connect to define an inner chamber 22 (FIG. 3) disposed there between. In one embodiment, the upper housing 18 and the lower housing 20 can be constructed as separate elements. When the upper housing 18 and the lower housing 20 are separate elements, the upper housing 18 and the lower housing 20 are joined together, and a seam 24 is formed between the upper housing 18 and the lower housing 20. When the upper housing 18 and the lower housing 20 are joined, an air tight seal is formed at the seam 24 between the upper housing 18 and the lower housing 20. In result, no gas can enter or escape the inner chamber 22 of the chemical pump housing 16 through the seam 24. In another embodiment, the upper housing 18 and the lower housing 20 could be integrally formed. Furthermore, the upper housing 18 may include an upper inner wall surface 26 which is only slightly curved and nearly planar, as depicted in FIG. 4. The lower housing 20 may include a lower inner wall 28 offset from the sidewalls of the lower housing 20.

Figure 3:
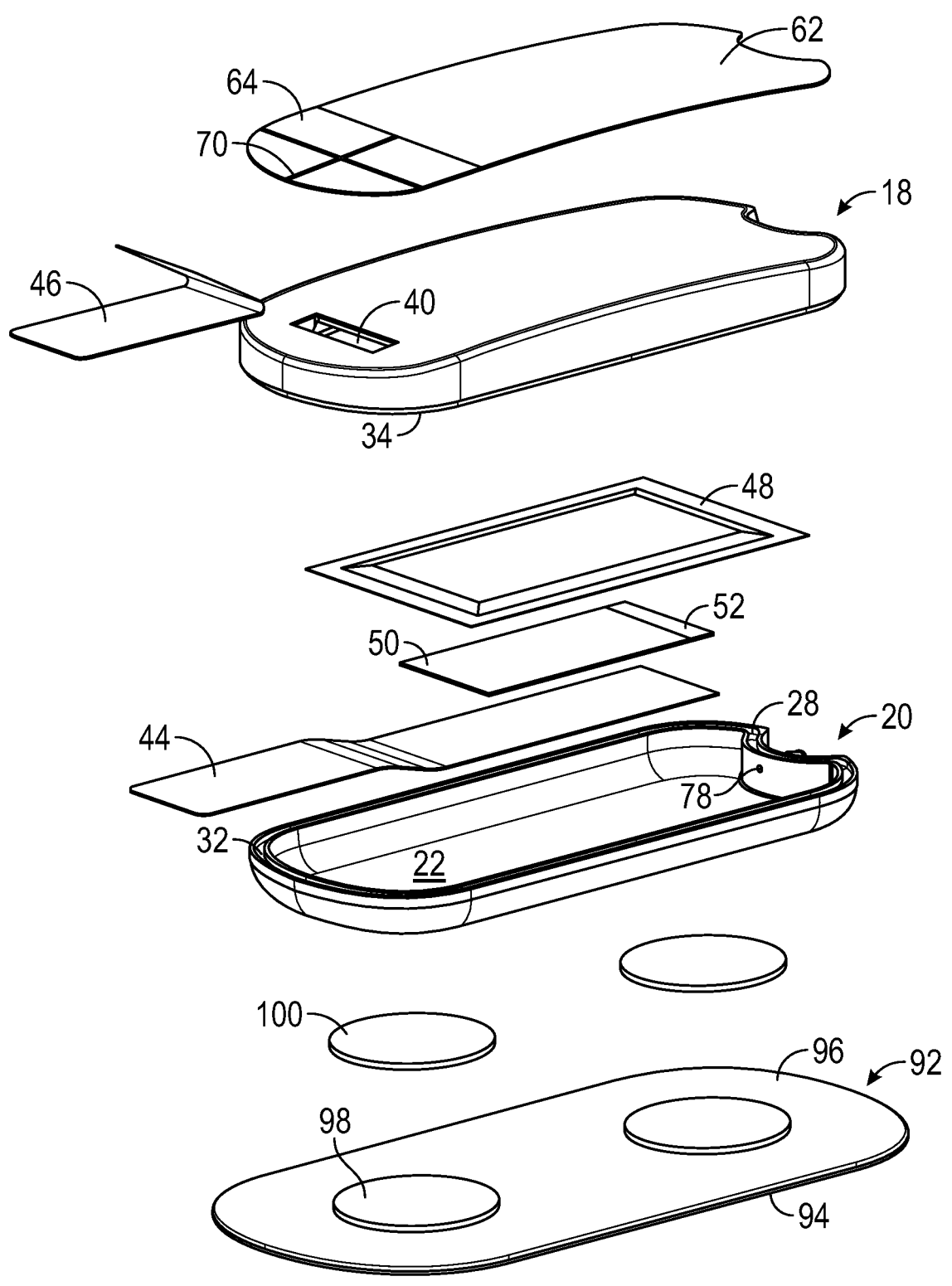
FIG. 3 is a perspective exploded view of the chemical pump assembly.
Figure 4:
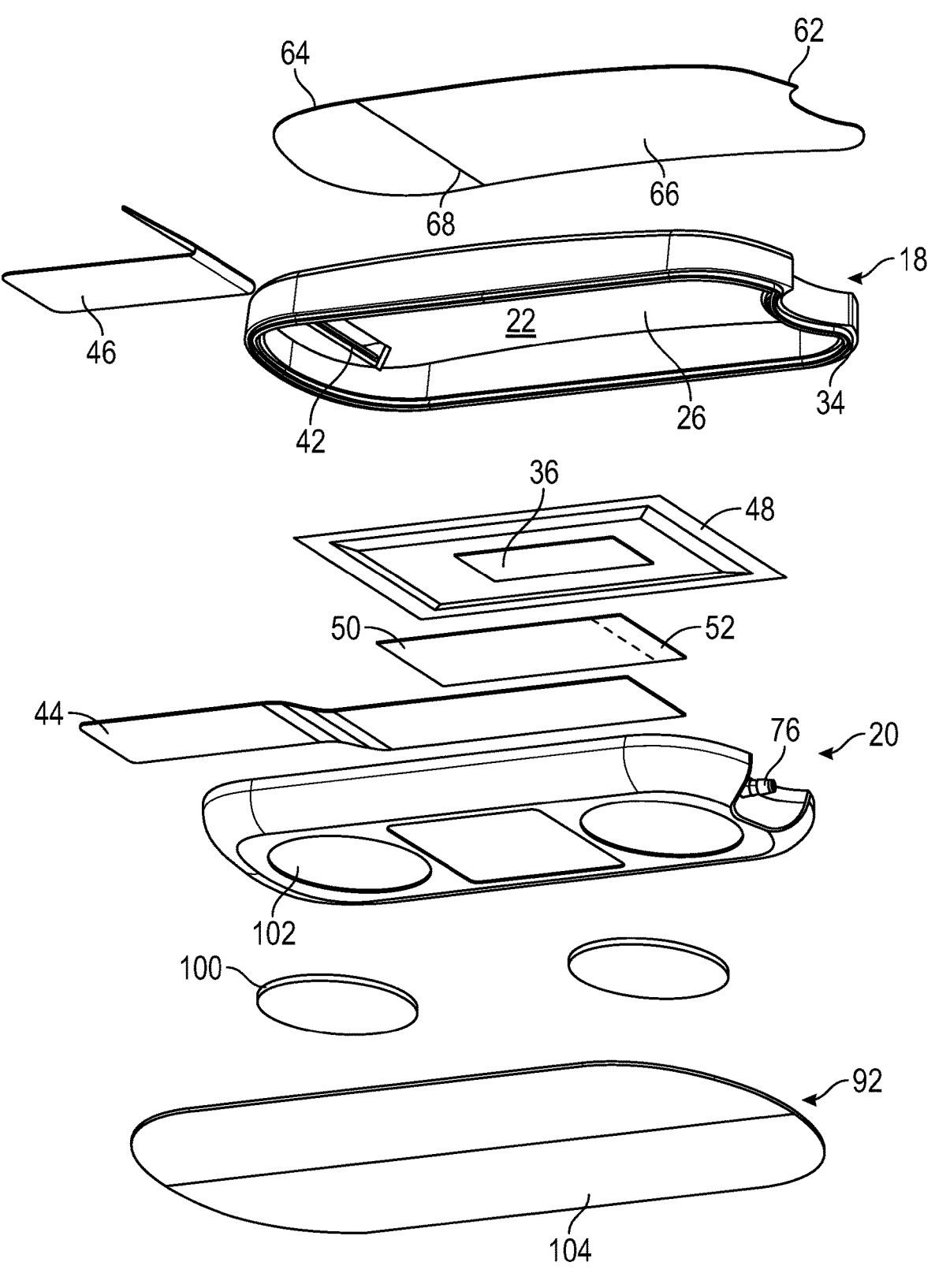
FIG. 4 is another perspective exploded view of the chemical pump assembly.

The lower housing 20 may further include a channel 32, as shown in FIG. 3, disposed around the inner periphery of the lower housing 20. The channel 32 may surround the entire inner periphery of the lower housing 20 or surround only a portion of the inner periphery of the lower housing 20. Furthermore, the channel 32 can be comprised of a single channel or multiple channels. The channel 32 may be disposed between the sidewalls of the lower housing 20 and the lower inner wall 28. On the upper housing 18, a ridge 34 may surround the inner periphery of the upper housing 18, as shown in FIG. 4. The ridge 34 may surround the entire inner periphery of the upper housing 18 or surround only a portion of the inner periphery of the upper housing 18. The ridge 34 can be comprised of a single ridge or multiple ridges. Alternatively, the ridge 34 may be disposed on the lower housing 20, and the channel 32 may be disposed on the upper housing 18.

The ridge 34 is configured to be inserted into the channel 32 when the upper housing 18 and the lower housing 20 are joined. When the ridge 34 is inserted into the channel 32, the upper housing 18 and the lower housing 20 can be welded and the air tight seal is created to prevent gas from passing through the seam 24. The upper housing 18 and the lower housing 20 can connect in other known manners to provide an air tight seal at the seam 24.

The chemical pump assembly 12 further includes a chemical pump 36 (FIG. 4). The chemical pump 36 is positioned in the inner chamber 22 of the chemical pump housing 16 prior to connecting the upper housing 18 and the lower housing 20. In the illustrated embodiment, the chemical pump 36 in the chemical pump assembly 12 is a reactor configured to chemically react with a selected gas, e.g., oxygen, found in air. Examples of reactors that can be used in the chemical pump assembly 12 are described in US 2014/0109890A1 and PCT/US2016/059364.

An opening 40, which is in the form of an elongate slit in the illustrated embodiment, is disposed on the upper housing 18. The opening 40 is preferably positioned towards a distal side of the upper housing 18. However, the opening 40 can be positioned towards a proximal section of the upper housing 18 as well as elsewhere on the chemical pump housing 16. When not covered, the opening 40 exposes the inner chamber 22 to ambient atmosphere. Adjacent the opening 40, the upper housing 18 can also include a sloped wall 42 that slopes upwardly and toward the distal side of the upper housing 18 from the inner chamber 22 toward the outer surface.

At least one pull tab extends from the inner chamber 22 to ambient through the opening 40, as shown in FIG. 2. In one embodiment, the at least one pull tab includes a first pull tab 44 and a second pull tab 46. In one embodiment, the first pull tab 44 and the second pull tab 46 are separate elements, whereas, in another embodiment, the first pull tab 44 and the second pull tab 46 could be connected or integral.

With reference to FIGS. 3 and 4, a packet 48 includes a removable layer 50 covering the chemical pump 36 so as to prevent the chemical pump 36 from being exposed to ambient atmosphere or air within the inner chamber 22 until after removal of the removable layer 50 from the packet 48. The packet 48 can be a foil packet that provides a hermetically sealed environment around the chemical pump 36. The first pull tab 44 extends through the opening 40 and is connected to removable layer 50. The first pull tab 44 can be pulled to remove the first pull tab 44 from the opening 40. When the first pull tab 44 is pulled through the opening 40, the removable layer 50 is removed from the packet 48 and, if desired, from the inner chamber 22 through the opening 40, exposing the chemical pump 36 to ambient atmosphere. After the removal of the removable layer 50, the chemical pump 36 begins to chemically react with a selected gas, e.g., oxygen, in the inner chamber 22. Since the wall 42 is sloped, the first pull tab 44 and the removable layer 50 are removed from the opening 40 with ease. The first pull tab 44 is preferably removed after the chemical pump assembly 12 is connected to the dressing 14. However, the first pull tab 44 can be removed prior to affixing the chemical pump assembly 12 to the dressing 14.

In the illustrated embodiment, the packet 48 is affixed to the upper inner wall surface 26 of the upper housing 18 through an adhesive. The packet 48 could be affixed to another surface, if desired. The removable layer 50 is coated on an upper side (per the orientation shown in FIG. 3) with an adhesive, with the exception of a small section 52 at and end of the removable layer 50 opposite from the opening 40, so as to adhere the removable layer 50 to the packet 48. The upper side of the removable layer being the side facing the packet 48. The first pull tab 44 connects with this small section 52, which lacks the adhesive, and the connection between the first pull tab 44 and the removable layer 50 is limited to the small section 52 in that the first pull tab 44 is free to move with respect to the remainder of the removable layer 50 that carries the adhesive on the upper side and is affixed to the packet 48. The removable layer 50 may be kiss cut (not through cut) to define a tear away section of the removable layer 50 and a remaining portion of the removable layer 50. As such, when the first pull tab 44 is pulled away from the chemical pump housing 16 through the opening 40, the removable layer 50 separates at the kiss cut, and the tear away section rolls over on itself as it is peeled away from the remaining portion and from the packet 48 to which the remaining portion is still adhered.

The chemical pump assembly 12 further includes a cover, an example of which being a thin film 62 described below, for sealing the opening 40 to prevent ingress of air through the opening 40 into the inner chamber 22 after the removable layer 50 has been removed. Other types of covers, e.g., films not already connected with the chemical pump housing 16, can also be employed.

The second pull tab 46 cooperates with the thin film 62, which is placed over and adhered to a portion of the top surface of the upper housing 18. The thin film 62 includes a flap 64 and, as depicted in FIG. 2, the opening 40 is disposed underneath the flap 64. The second pull tab 46 is connected to a release layer 66 provided on a bottom surface of the thin film 62. The release layer 66 covers an adhesive (not visible in FIG. 2) on the bottom surface of the thin film 62. With reference to FIG. 4, a slit 68 is provided in the release layer 66 so that one section of the release layer 66 is removed exposing the adhesive prior to affixing the thin film 62 to the top surface of the upper housing 18, while the portion of the release layer 66 beneath the flap 64 can remain. When the second pull tab 46 is pulled, the second pull tab 46 disconnects the release layer 66 from the flap 64 and the adhesive disposed on the bottom surface of the flap 64 is exposed. The flap 64 is then moved towards the upper housing 18 to cover the remainder of the top surface of the upper housing 18 and thus also covers the opening 40. In result, the inner chamber 22 is no longer exposed to ambient atmosphere via the opening 40. In the illustrated embodiment, the thin film 62 is metallized to prevent the ingress of air into the inner chamber 22 when the inner chamber 22 is at negative pressure. In order to prevent the ingress of air, the thin film 62 may be a metalized polymer film including a metal layer arranged on a polymer film (e.g. polyester, polyethylene, polypropylene, polylactic acid, polyimide, fluoropolymer, polyether ether ketone, polyvinylidene chloride, ethylene vinyl alcohol, nylon, polyethylene terephthalate). The metal may be a foil or coating layer, and may have a thickness of, for example, from 10 nm to 10 μm. The metal layer may include various metals, for example aluminum, nickel, copper, or chromium. The metal layer may be laminated with or coated on the polymer film. Coating of the metal layer on the polymer film may be accomplished by various deposition techniques, such as physical vapor deposition including a variety of vacuum deposition methods. The metalized polymer film may include further layers, such as a protection layer over the metal layer.

Figure 5:
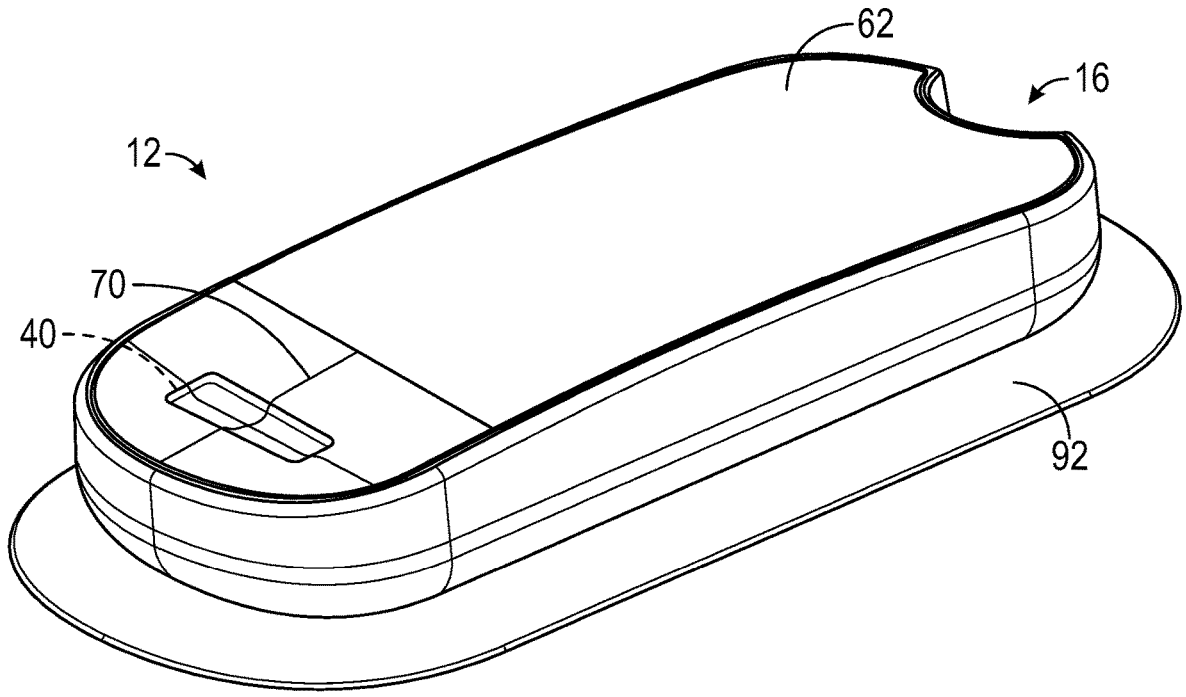
FIG. 5 is a perspective view of the chemical pump assembly after a first pull tab and a second pull tab have been removed.

When the thin film 62 covers the opening 40, the chemical pump 36 chemically reacts with the selected gas found in the enclosed volume under the dressing, and if already connected to the dressing via a hose 82 (shown schematically in FIGS. 1 and 7, and in phantom in FIG. 6) creates a closed system. Reduced pressure is therefore developed within the enclosed volume. When the inner chamber 22 is under negative pressure, the thin film 62 is drawn in through the opening 40 toward the inner chamber 22 (See FIG. 5). As such, the thin film 62 cooperating with the opening 40 can provide an indication to the user that the inner chamber 22 is under negative pressure. Indicia 70, e.g. lines, a cross or the like, can also be provided on the thin film 62 in the vicinity of the opening 40 to provide further indication of negative pressure.

The chemical pump housing 16 further includes a hose fitting 76, which in the illustrated embodiment is a barbed fitting to secure fixation of the hose 82 to the hose fitting 76. The hose fitting 76 is tubular and includes a passage 78 in communication with the inner chamber 22. In one embodiment, the hose fitting 76 is disposed on the opposite side of the chemical pump housing 16 as the opening 40. The hose fitting 76 may be disposed on a concave section 80 of the chemical pump housing 16; however, the hose fitting 76 may be disposed on any surface of the chemical pump housing 16. The concave section 80 can be alternatively disposed on any surface of the chemical pump housing 16. The hose 82 (schematically depicted) attaches to the hose fitting 76 to connect the chemical pump assembly 12 to the dressing 14.

With reference back to FIG. 1, the chemical pump assembly 12 can further include an attachment pad 92 disposed underneath and connected with the lower housing 20. The attachment pad 92 includes a lower side 94 and an upper side 96. Fasteners, e.g. hook and loop fasteners, 98 may be disposed on the upper side 96 of the attachment pad 92 for connection with hook and loop fasteners 100 received inside recesses 102 provided in a bottom surface of the lower housing 20 to affix the attachment pad 92 to the chemical pump housing 16. The attachment pad 92 may be larger than the chemical pump housing 16. The lower side 94 of the attachment pad 92 is configured to attach to a surface, e.g. a gown or clothing worn by a patient, or the patient. The attachment pad 92 may include an adhesive layer disposed on the lower side 94. A removable attachment pad release liner 104 can be disposed on the adhesive. The removable attachment pad release liner is removed to expose the adhesive.

A method for operating the chemical pump assembly 12 will be described hereinafter. At least one dressing 14 can be placed over a tissue site and sealed to tissue surrounding the tissue site to thereby define the enclosed volume between the dressing and the tissue. The chemical pump assembly 12 can then connect to the at least one dressing 14 via the hose 82. When the chemical pump assembly 12 is connected to the at least one dressing 14 via the hose 82, the inner chamber 22 of the chemical pump assembly 12 is in fluid communication with the enclosed volume defined by the dressing 14. That is, the hose 82 is connected to the dressing 14 and to the housing 12 to at least partially define a fluid passage between the enclosed volume and the inner chamber 22. The desired amount of oxygen to be attained in the enclosed volume can be controlled by adjusting a length of the hose 82; adjusting a cross-sectional area of the hose 82; or covering a portion of the dressing 14 with a cover layer 15 having a permeability to air less than the dressing 14.

Either pull tab 44 or 46 can be pulled. When the first pull tab 44 is pulled through the opening 40 the removable layer 50 is removed from the packet 48. In result, the chemical pump 36 in the chemical pump housing 16 is exposed to ambient atmosphere as well as air in the inner chamber 22 and begins to react with a selected gas. The second pull tab 46 is pulled to remove the release layer 66 provided on a bottom surface of the flap 64 to expose adhesive on the bottom surface. The flap 64 is then brought toward the upper housing 18 to cover the opening 40 with the thin film 62. As a result, the inner chamber 22 is no longer exposed to ambient atmosphere. The reactor (chemical pump 36) then chemically reacts with the selected gas in the inner chamber 22 and the enclosed volume beneath the dressing 14 and applies reduced pressure at the tissue site.

Figure 6:
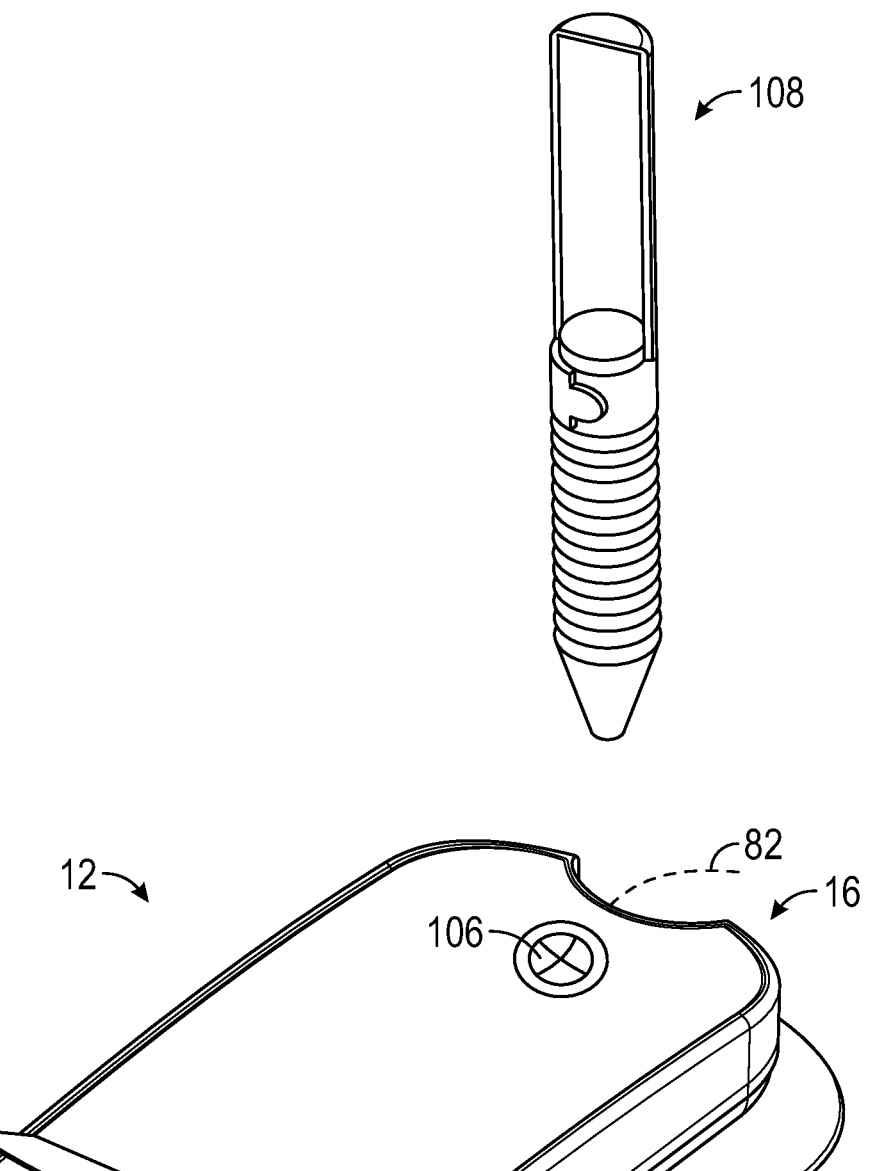
FIG. 6 is a perspective view of a chemical pump assembly including a valve.

FIG. 6 depicts the chemical pump housing 16 including a valve, which can be a bidirectional valve 106. Note, the chemical pump 36 and packet 48 may need to be reduced in size or the size of the chemical pump housing 16 may need to be enlarged to accommodate the bidirectional valve 106. The bidirectional valve 106 may be similar in construction to the valve described in U.S. Pat. No. 5,439,143. The bidirectional valve 106 can be configured such that (1) when the air pressure external to the bidirectional valve 106 is below the air (or gas pressure) of the inner chamber 22 the bidirectional valve 106 opens and air is allowed to be drawn from the inner chamber 22 through the bidirectional valve 106, (2) when the ambient air pressure is more than a predetermined differential (e.g., 200 mm Hg) greater than the air (or gas pressure) of the inner chamber 22 the bidirectional valve 106 opens and air is allowed to enter the inner chamber 22 through the bidirectional valve 106, and (3) in other instances the bidirectional valve 106 remains closed so as to prevent air from entering or exiting the inner chamber 22 through the bidirectional valve 106. It is in this third state in which the inner chamber 22, and therefore the enclosed volume beneath the dressing, is in a therapeutic range, e.g., between −40 mmHg to −200 mmHg offset from ambient atmosphere (e.g., absolute pressure of 560 to 710 mmHg at sea level). If desired, a mechanical pump assembly 108, which is more particularly described in PCT/US19/12298, can be inserted into the bidirectional valve 106, thus opening the valve, and activated to provide negative pressure to the enclosed volume beneath the dressing 14 when the chemical pump assembly 12 is connected with the dressing via the hose 82. Also, conventional wall suction pumps, sometimes referred to as "wall suction," can also connect with the bidirectional valve 106, thus opening the valve to provide negative pressure to the enclosed volume beneath the dressing 14 when the chemical pump assembly 12 is connected with the dressing via the hose 82.

Instead of the bidirectional valve 106, two one-way valves could also be employed. One of the one-way valves can be configured such that when the air pressure external to the one-way valve is below the air (or gas pressure) of the inner chamber 22 the one-way valve opens and gas is allowed to be drawn from the inner chamber 22 through the one-way valve. The other one-way valve can be configured such that when the ambient air pressure is more than a predetermined differential (e.g., 200 mm Hg) greater than the air (or gas pressure) of the inner chamber 22 this one-way valve opens and air is allowed to enter the inner chamber 22 through the one-way valve. Both one-way valves would remain closed when the inner chamber 22 is in a therapeutic range, e.g., between −40 mmHg to −200 mmHg offset from ambient atmosphere (absolute pressure of 560 to 710 mmHg at sea level). The mechanical pump assembly 108, wall suction or similar mechanical suction device could cooperate with the one-way valve that allows air to enter the inner chamber 22.

The amount of oxygen in the enclosed volume, which is defined between the dressing 14 and the skin S, will be determined based on the flow of oxygen through a fluid passage (i.e. fluid passage conductance) from the enclosed volume to the inner chamber 22, and the permeation of oxygen from the surrounding environment, through the exposed surface of the dressing 14, and into the enclosed volume. Thus, the amount of oxygen in the enclosed volume, which is a function of the amount of oxygen permeating through the dressing 14, may be controlled by adjusting the area of the dressing 14 that is covered by the cover layer 15. Further, the amount of oxygen in the enclosed volume, which is a function of the fluid passage conductance, may be controlled by adjusting the length of the fluid passage and adjusting the smallest cross-sectional area of the fluid passage.

Figures 7, 8:
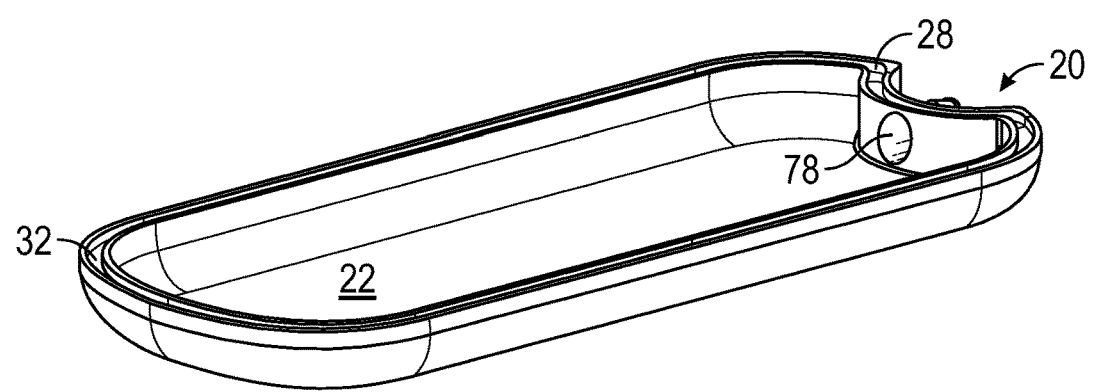
FIG. 7 is a perspective view of a chemical pump assembly fluidly connected to a dressing.
FIG. 8 is a perspective view of a lower housing of a chemical pump assembly.

With reference to FIGS. 7-8, the fluid passage between the enclosed volume and the inner chamber 22 may be cumulatively defined by the hose fitting 76, the hose 82, and a dressing fitting 84 on an ambient-exposed surface of the dressing 14. If this flow of oxygen increases through the fluid passage (which is driven by the consumption of oxygen by the chemical pump 36), the amount of oxygen in the enclosed volume may decrease. The flow of oxygen from the enclosed volume to the inner chamber 22 as driven by the partial pressure gradient of oxygen between the inner chamber 22 and the enclosed volume, may be a function of the smallest cross-sectional area (taken normal to a length) of the fluid passage between the enclosed volume and the inner chamber 22, and also a function of a length of the fluid passage. The conductance of the fluid passage depends on all the cross-section areas, not just the smallest, and, of course, the length of the segment of each particular area. The flow or diffusion of $O_2$ through the tubing is driven by the pressure gradient between the enclosed volume and the inner chamber, restricted by the resistance of the fluid passage to the flow. The fluid passage can be regarded as having three or more sections with different resistances to flow: the resistance of the hose fitting 76 ($R_1$), the resistance of the hose 82 ($R_2$), and the resistance of the dressing fitting 84 ($R_3$). If a restriction is placed on a portion of the hose 82 to decrease its cross section in a particular, there may be a fourth section with a different resistance to flow ($R_4$), which may be zero if there is no additional restriction on the hose 82. The total resistance of the fluid passage to flow will be the sum of the resistances of the individual sections (just as an electrical resistance of a circuit of resisters in series equals the sum of the individual resisters) and may be represented as follows:

$$R_{total}=R_1+R_2+R_3+R_4$$

The resistance to flow $R_i$ is proportional to the fluid passage's length $l_i$ divided by its cross-sectional area $A_i$: $R_i \propto l_i/A_i$. The rate of flow is proportional to the fluid passage's conductance $G=1/R$, so:

$$G=1/R_{total} \propto 1/(R_1+R_2+R_3+R_4)$$

The relative magnitudes of the $R_i$'s will determine whether or not one Ri dominates the conductance G. If the length of the smallest cross-section area is short enough, the resistance of the rest of the tubing may still dominate, although less so than without the clamp.

As will be appreciated, the smallest cross-section area anywhere along the length of the fluid passage may, to a large extent, be a limiting factor to flow, e.g. through a bottleneck effect, for the fluid passage conductance even though other portions of the fluid passage have larger internal cross-sectional areas. Therefore, a change in the smallest cross-sectional area of the fluid passage and/or a change in the total length of the fluid passage, or a change in the cross-sectional area of the rest of the fluid passage, will produce a change in the flow of oxygen from the enclosed volume to the chemical pump 36, and thus produce a corresponding change in the amount of oxygen in the enclosed volume around a tissue site. If the dressing is rigid, a reduction in the amount of oxygen in the enclosed volume may produce a change in pressure in the enclosed volume, i.e. it may produce a negative pressure in the enclosed volume.

The present invention thus provides a system for negative pressure and hypoxic tissue therapy, which allows a user to select the smallest cross-sectional area of the fluid passage and/or a length of the fluid passage, in order to produce a desired amount of oxygen in the enclosed volume, which corresponds to one of various predetermined amounts of oxygen in the enclosed volume.

FIG. 7 depicts a chemical pump assembly 12, which is similar to that described herein with respect to FIGS. 1-6, but with a variation as to the size of the hose fitting 76 and corresponding passage 78, and the dressing fitting 84 and corresponding opening 85 to the enclosed volume. As depicted, the hose fitting 76 has a larger internal cross-sectional area (i.e. the cross-sectional area of the passage 78) than that depicted in FIGS. 1 and 3-4, and the dressing fitting 84 has a larger internal cross-sectional area (i.e. the cross-sectional area of the opening 85) than that depicted in FIGS. 1 and 3-4. The larger hose fitting 76 and dressing fitting 84 can be used with a hose 82 having a corresponding increased internal cross-sectional area, which may be equal to the internal cross-sectional area of the hose fitting 76 (i.e. the cross-sectional area of the passage 78) and the internal cross-sectional area of the dressing fitting 84 (i.e. the cross-sectional area of the opening 85). One end of the hose 82 may be connected to the hose fitting 76, and the other end of the hose 82 may be connected to the dressing fitting 84.

The hose fitting 76, the hose 82, and the dressing fitting 84 may collectively define the fluid passage between the inner chamber 22 of the chemical pump assembly 12 and the enclosed volume defined by the dressing 14 and the skin S. The hose 82 may be connected to the hose fitting 76 and dressing fitting 84 by ends of the hose 82 being fitted around the hose fitting 76 and dressing fitting 84. This connection may be accomplished with a compression fit between the internal surface of the hose 82 and the external surfaces of the hose fitting and dressing fitting 84. The hose fitting 76 and dressing fitting 84 may also be barbed on their outer surfaces to thus seal to the inside surface of the hose 82 and inhibit removal of the hose 82 therefrom. In this scenario, the internal cross-sectional area of either the hose fitting 76 or dressing fitting 84 may be smaller than the internal cross-sectional area of the hose 82 so that the ends of the hose 82 can be fitted around the hose fitting 76 and dressing fitting 84, and thus these may define the smallest cross-sectional area of the fluid passage between the enclosed volume and the inner chamber 22. Alternatively, each end of the hose 82 may be slightly expanded to have a larger internal cross-sectional area than a central portion of the hose 82, to therefore allow the ends of the hose 82 to be connected to the hose fitting 76 and dressing fitting 84 by being fitted around the hose fitting 76 and dressing fitting 84. In this alternative scenario, the internal cross-sectional area of the central portion of the hose 82 may be the same as the internal cross-sectional area of both the hose fitting 76 and dressing fitting 84. As such, the smallest cross-sectional area of the fluid passage between the enclosed volume and the inner chamber 22 may be defined by each of the central portion of the hose 82, the hose fitting 76, and the dressing fitting 84 because they all have the same internal cross-sectional areas.

The hose 82 may also be connected to the hose fitting 76 and dressing fitting 84 by being fitted inside the hose fitting 76 and dressing fitting 84. This connection may be accomplished with a compression fit forming a seal between the external surface of the hose 82 and the internal surfaces of the hose fitting and dressing fitting 84. In this scenario, the internal cross-sectional area of the hose 82 may be smaller than the internal cross-sectional area of either the hose fitting 76 and dressing fitting 84, and thus this may define the smallest cross-sectional area of the fluid passage between the enclosed volume and the inner chamber 22.

The hose 82 may also be connected to the hose fitting 76 and dressing fitting 84 by being butted up against the hose fitting 76 and dressing fitting 84. This connection may be accomplished by using two connector sheaths, into which the ends of the hose 82 and each of the hose fitting 76 and dressing fitting 84 are arranged such that the connector sheath surrounds each end of the hose 82 and the hose fitting 76 and the dressing fitting 84 and creates a compressing fit therewith. In this scenario, the internal cross-sectional area of the hose 82 may be the same as the internal cross-sectional area of both the hose fitting 76 and dressing fitting 84, and thus the smallest cross-sectional area of the fluid passage between the enclosed volume and the inner chamber 22 is defined by each of the hose 82, hose fitting 76, and dressing fitting 84.

In any event, the smallest cross-sectional area of the fluid passage is expanded to be larger than that shown in FIGS. 1, 3-4. As such, the fluid passage conductance (i.e. the flow of the selected gas, e.g. oxygen, from the enclosed volume to the inner chamber 22) will increase as compared to when the smallest cross-sectional area of the fluid passage is smaller, e.g. as shown in FIG. 1, 3-4, and thus the flow of oxygen from the enclosed volume to the inner chamber 22 can be increased.

Figure 9:
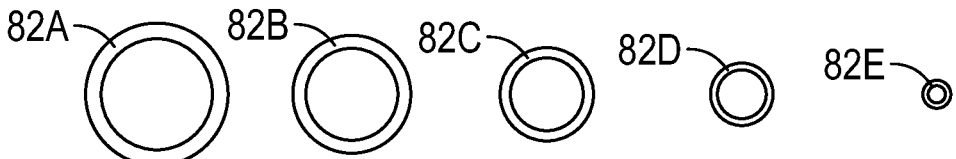
FIG. 9 are cross-sectional views of various size hoses to connect to a chemical pump assembly.

As will be appreciated, the cross-sectional areas of the passage 78 and opening 85 may be fixed, and thus the smallest internal cross-sectional area of the hose 82 that is used may determine the effective cross-sectional area of the fluid passage. The flow of oxygen through the fluid passage may thus be determined based on the smallest internal cross-sectional area of the hose 82 that is selected. FIG. 9 shows various hoses 82A-82E having different sizes with varying internal cross-sectional areas taken normal to their lengths, each of which may be selectively used to connect the chemical pump assembly 12 to the dressing 14. The size of the hose 82 used may determine the flow of oxygen, and thus may determine the amount of oxygen in the enclosed volume. As such, one of these hoses 82A-82E may be selectively chosen by a user to provide predetermined amounts of oxygen in the enclosed volume under the dressing 14. The larger the internal cross-sectional area of the hose that is used, the more oxygen that may flow therethrough, and the more oxygen that may be consumed by the chemical pump 36. This is because the larger the internal cross-sectional area of the hose, the more oxygen can flow from the enclosed volume under the dressing 14 to the chemical pump 36 in the chemical pump assembly 12, and the less oxygen may remain in the enclosed volume under the dressing 14. The option to use different size hoses 82A-82E thus may provide an opportunity for a user to selectively alter the amount of oxygen around a wound in the skin S.

Figure 10:
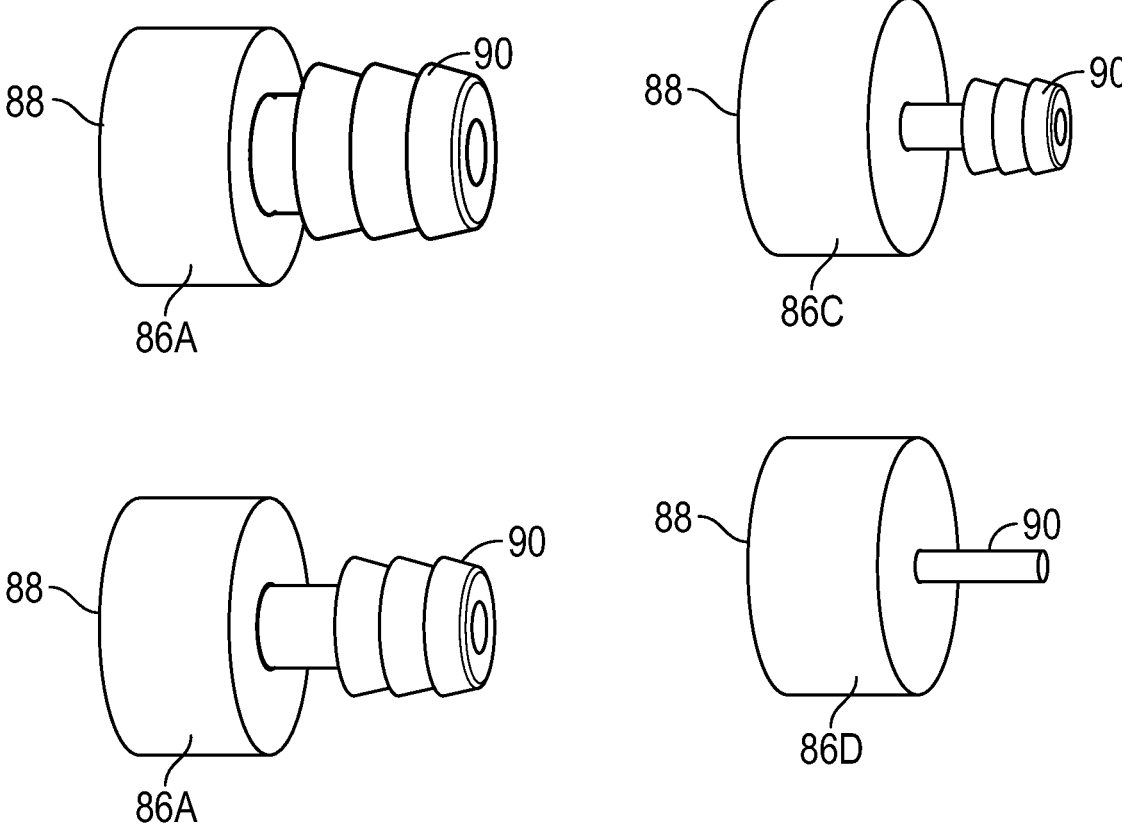
FIG. 10 are perspective views of various size adaptors for use with the hoses of FIG. 9.

The various size hoses 82A-82E may be directly connected to the hose fitting 76 and dressing fitting 84, or may be connected to these via one or more adaptors 86A-86D a depicted in FIG. 10, which have a channel extending therethrough from a tip 90 to a base 88. For example, the largest hose 82A may have the same internal cross-sectional area as the passage 78 and the opening 85, and may thus be connected (as described above) directly to these without the use of one of the adaptors 86A-86C. However, the smaller hoses 82B-82E may have internal cross-sectional areas that are less than those of the hose fitting 76 and dressing fitting 84, and may thus be connected to each of these via the adaptors 86A-86D (or otherwise as described above), where one adaptor 86A-86D is connected to each of the hose fitting 76 and dressing fitting 84 by putting the base 88 of one adapter over the hose fitting 76, and the base 88 of another adapter over the dressing fitting 84, and by putting the ends of the corresponding hose 82B-82E around, inside, or abutted to, the tip 90 of each adapter. For example, hose 82B may be connected via two adaptors 86A to each of the hose fitting 76 and dressing fitting 84, hose 82C may be connected via two adaptors 86B to each of the hose dressing fitting 76 and fitting 84, hose 82D may be connected via two adaptors 86C to each of the hose fitting 76 and dressing fitting 84, and hose 82E may be connected via two adaptors 86D to each of the hose fitting 76 and dressing fitting 84. The adaptors 86A-86D may thus allow different size hoses 82A-82E to be connected to the standard size hose fitting 76 and dressing fitting 84, which themselves may have fixed internal cross-sectional areas.

As will be appreciated, the smaller the internal cross-sectional area of the hose 82 that is used to connect the hose fitting 76 to the dressing fitting 84, the less amount of oxygen that may flow from the enclosed volume to the chemical pump 36, and the more amount of oxygen may remain in the enclosed volume. As such, by using different size hoses 82A-82E, a user may be able to selectively choose the amount of oxygen that remains in the enclosed volume.

Figure 11:
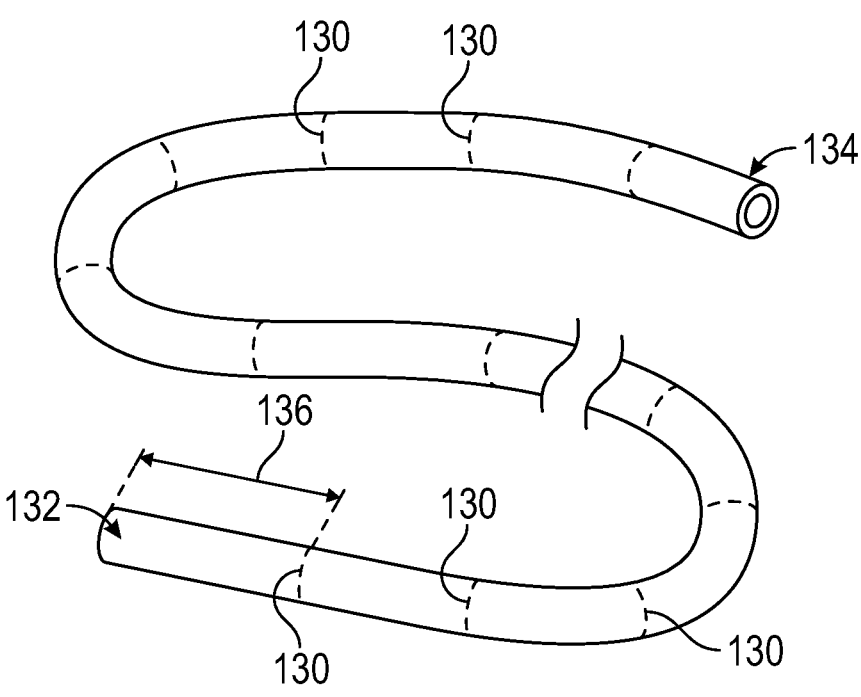
FIG. 11 is a perspective view of a hose with markings.

Besides selecting the cross-sectional area of the hose 82 to control the amount of oxygen in the enclosed volume, a user may also/alternatively selectively alter a length of the hose 82 that is used. FIG. 11 depicts a hose 82 having a length, and including various markings 130 along the length of the hose 82 from a first end 132 to a second opposite end 134. These markings 130 may indicate a location to selectively sever (e.g. cut) the hose 82 to make it shorter than the original length. Cutting the hose at one of the markings 130 may provide various predetermined lengths for the hose 82. In conjunction with other variables such as smallest internal cross-sectional area of the hose 82, these various predetermined lengths may correspond to predetermined levels oxygen to be attained in the enclosed volume, which correspondence may be determined through testing. As the length of the hose 82 is selectively reduced from the original length, the flow of oxygen through the hose 82 from the enclosed volume to the inner chamber 22 may increase, and thus the amount of oxygen remaining in the enclose volume may correspondingly be decreased. The markings 130 may be arranged on the hose 82 so as to indicate predetermined amounts (e.g. percentage amounts) by which the flow of oxygen may increase through the hose 82 from that provided by the original length of the hose. These markings 130 may be included on any of the hoses 82A-82E. By these markings 130, a user may be able to select, along with a cross-sectional area of the hose, a desired amount of oxygen to be in the enclosed volume that corresponds to a predetermined amount of oxygen in the enclosed volume.

The flow of oxygen through a large hose (e.g. hose 82A) or through a short hose (e.g. a hose having a single segment length 136 from the first end 132 to the closest marking 130 or shorter) may primarily include a bulk flow of oxygen, while the flow of oxygen through a small hose (e.g. hose 82E) or through a long hose (e.g. a hose having the original length) may primarily include diffusion of oxygen, which is generally less than a bulk flow of oxygen. Hoses between these sizes (e.g. hoses 82B-82D, and hoses having a length longer than the single segment length 136) may have a flow including gradient amounts of bulk flow and diffusion, which correspond to their relative internal cross-sectional areas and lengths and which can be selected by a user.

Figure 12:
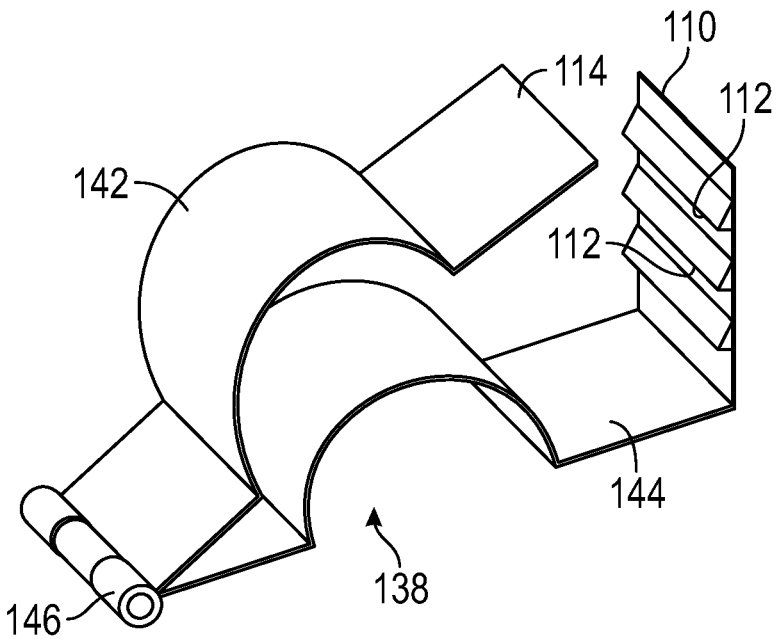
FIG. 12 is a perspective view of a clamp for sealing a hose.
Figure 13:
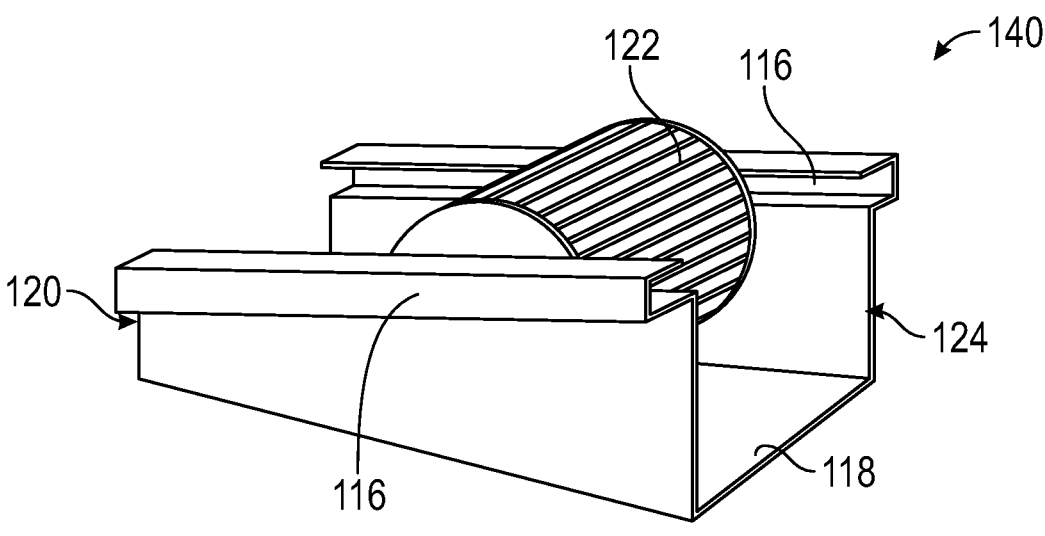
FIG. 13 is a perspective view of another clamp for sealing a hose.

Clamps may be used to selectively prevent the flow of oxygen through the hose 82. FIGS. 12 and 13 depict two clamps 138, 140, which may be used to seal the hose 82 to prevent the flow of oxygen therethrough. The clamps are not limited to those shown in FIGS. 12 and 13, and other clamps or mechanisms may be used to seal the hose 82.

The hose 82 may be clamped when exchanging an old chemical pump assembly 12 for a new one, when exchanging an old dressing 14 with a new one, each of which may require disconnection from the hose 82 from the old ones, or when a desired oxygen amount is attained in the enclosed volume. The clamps 138, 140 may thus be used to seal off the environment in the enclosed volume and to seal off the environment in the inner chamber 22. After removing the old chemical pump from the hose 82, it can be replaced with a new chemical pump 12, which can then be fluidly connected to the enclosed volume by releasing the hose 82 from the clamp. After removing the old dressing 14 from the hose 82, it may be replaced with a new dressing 14, which can then be fluidly connected to the inner chamber 22 by releasing the hose 82 from the clamp.

The clamp 138 may include a first portion 142 and a second portion 144 that are rotationally connected at a hinge 146, and between which the hose 82 can be arranged. The first portion 142 and second portion 144 may be brought together to cinch the hose 82 between then in order to stop the flow of oxygen through the hose 82. The second portion 144 may include a flange 148 having barbs 112, which engage a tip 114 of the first portion 142 to lock the clamp 138 around the hose 82 and seal off the flow of oxygen through the hose 82. The hose 82 may be release from the clamp 138 by pushing on the flange 110 so the barbs 112 no longer engage the tip 114.

The clamp 140 may include channels 116, which converge towards a base 118 going towards a first end 120 of the clamp 140, and in which pins (not shown) extending from either side of a roller 122 are guided when the roller 122 is moved with respect to the base 118. The hose 82 can be arranged between the roller 122 and the base 118. When the roller 122 is at the second end 124 of the clamp 140, the roller 122 may not cinch the hose 82 and the flow of oxygen therethrough may not be diminished. However, when the roller 122 is moved to the first end 120 of the clamp 140, the roller 122 may cinch the hose 82 and prevent the flow of oxygen therethrough.

Figure 14:
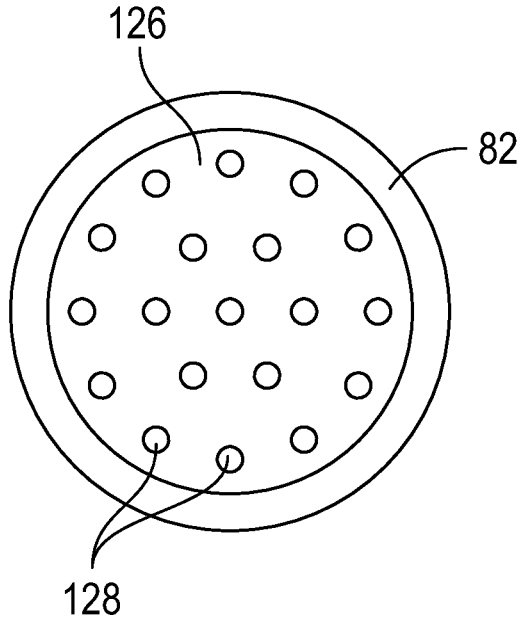
FIG. 14 is a cross-sectional view of a hose with a porous solid.

FIG. 14 depicts a porous solid 126 arranged inside the hose 82. The porous solid 126 may be a material that limits the bulk flow of oxygen through the hose 82. The porous solid 126 may be included when it is desired that the flow of oxygen include more diffusion of oxygen than would otherwise be present without the inclusion of the porous solid 126. The porous solid 126 is schematically depicted to include pores 128. However, such pores 128 may or may not be visible to the naked-eye. Some or all of the pores 128 may be of a size to only allow diffusion of oxygen through the porous solid 126, while some or all of the pores 128 may be of a size to allow the bulk flow of oxygen through the porous solid 126.

Besides selecting the cross-sectional area of the hose 82 and selectively altering a length of the hose 82 that is used in order to control the amount of oxygen in the enclosed volume, a user may also or alternatively cover the dressing 14, or a portion thereof, with a cover layer 15 (FIG. 7). The cover layer 15 may be less permeable to air, e.g. oxygen, nitrogen, etc., than the dressing 14 without the cover layer 15. In this regard, the dressing 14 may be at least partially permeable to air. The cover layer 15 may be impermeable to air.

The impermeable cover layer 15 may be sealed to a an exposed surface of the dressing 14 as shown in FIG. 7, to thereby define a covered portion of the dressing 14. The covered portion of the dressing 14 may include the entire dressing 14, or only a portion thereof. The cover layer 15 thus makes the covered portion of the dressing 14 impermeable to air, and thus impermeable to oxygen. The cover layer 15 inhibits the permeability of oxygen from the surrounding environment and into the enclosed volume, by providing the covered portion of the dressing 14 with the characteristic of being impermeable to oxygen.

As will be understood, the larger the area of the cover layer 15 with respect to the area of the dressing, the more inhibition to oxygen permeation through the dressing 14 will be provided. In other words, a relatively larger cover layer 15 will cover more area of the dressing 14 and thus will inhibit the permeation of oxygen through the dressing and into the enclosed volume, more than would a relatively smaller cover layer 15. As such, the larger the cover layer 15, the less permeation of oxygen through the dressing 14; while the smaller the cover layer 15, the more permeation of oxygen through the dressing 14. In FIG. 7, various dotted lines are shown on the cover layer 15 indicating various sizes for the cover layer 15, or indicating predefined cutting lines for selectively modifying an original size of the cover layer 15 so that is can be made smaller than the original size to attain a desired amount of permeation of oxygen into the enclosed volume.

Limiting the permeability of air through the covered portion of the dressing 14 will limit the amount of oxygen entering into the enclosed volume. This limitation, in combination with the flow of oxygen out of the enclosed volume, through the tube 82, and into the inner chamber 22 to be consumed by the chemical pump 36 (reactor), will provide a reduced level of oxygen in the enclosed volume and around a tissue site. As such, the cover layer 15 will provide a lower level of oxygen in the enclosed volume than if the cover layer 15 were not used, since the cover layer 15 is impermeable to oxygen. In this way, the cover layer 15 offers another level of control to a user for adjusting the amount of oxygen around the tissue site.

The cover layer 15 may have a size (i.e. area) that can be selected by a user in order to provide a certain amount of oxygen around the tissue site. This size may be a predetermined size that corresponds to a predetermined amount of oxygen being in the enclosed volume and around the tissue site. A cover layer 15 having the predetermined size may be selected from a plurality of cover layers having different predetermined sizes, or may be selected by selectively altering an original size of the cover layer 15, such as by cutting the cover layer 15 to make it smaller.

The cover layer 15 may include various material for this purpose, including a base polymer film coated or filled with a material that decrease the transmission rate of air through its thickness, and these coating or filling materials may include blocking materials of metal, graphene, polyvinylidene chloride, polyvinyl alcohol, ethylene vinyl alcohol, or combinations thereof. The base polymer film to be coated or filled with these blocking materials may include high density polyethylene, polyethylene terephthalate, polylactic acid, polypropylene, polystyrene, etc., or combinations thereof. The cover layer 15 may also include additional layers to form a multilayer structure including additional layers, which may include these blocking materials. The cover layer 15 may be a metalized polymer film similar to that as described herein for the thin film 62.

The cover layer 15 may include a sealant for adhering the cover layer 15 to the exposed surface of the dressing 14. The sealant may be arranged on the bottom surface of the cover layer 15. The sealant may include adhesives, hydrogel material, silicone material (e.g. silicone gel), or any other material that can inhibit the migration of air. The sealant may have the same permeability to air as the other materials of the cover layer 15. The sealant may be resealable to allow for sealing the cover layer 15 to the dressing 14, and then also for later removal of the cover layer 15 from the dressing 14.

The amount of oxygen present in the enclosed volume is dependent on the balance between the amount of oxygen being conducted through the fluid passage from the enclosed volume to the inner chamber 22, and the amount of oxygen being transmitted from the surrounding environment, through the dressing 14, and into the enclosed volume. Thus, selecting the length and smallest internal cross-sectional area of the fluid passage, along with selecting the area of the dressing 14 to be covered by the cover layer 15, will determine the amount of oxygen that is present in the enclosed volume. If relatively more oxygen is desired to be in the enclosed volume, then the length of the fluid passage can be selected to be large, the smallest internal-cross sectional area of the fluid passage can be selected to be tiny, and/or a small area, or none, of the dressing 14 can be covered by the cover layer 15. If less oxygen is desired to be in the enclosed volume, then the length of the fluid passage can be selected to be small, the smallest internal-cross sectional area of the fluid passage can be selected to be large, and/or a large area of the dressing 14 can be covered by the cover layer 15.

It will be appreciated that various of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A system for controlling an amount oxygen in an enclosed volume, the system comprising:
   a dressing configured to seal to tissue so as to define the enclosed volume between the dressing and the tissue;

a housing defining an inner chamber, and including a reactor located in the inner chamber, the reactor being configured to chemically react with oxygen in the inner chamber;

a fluid passage connecting the inner chamber and the enclosed volume allowing for a flow of oxygen between the inner chamber and the enclosed volume; and a plurality of hoses having different lengths, wherein the system is configured to allow a user of the system to select a predetermined level of oxygen to be attained in the enclosed volume by the user:

selecting a desired length of the fluid passage among a plurality of different lengths prior to the reactor being exposed to oxygen in the inner chamber, wherein the desired length corresponds to the predetermined level of oxygen to be attained in the enclosed volume, and selecting the desired length of the fluid passage includes selecting one hose from the plurality of hoses having the desired length, and connecting the one hose to the housing and to the dressing to at least partially define the fluid passage.

2. A system for controlling an amount oxygen in an enclosed volume, the system comprising:
   a dressing configured to seal to tissue so as to define the enclosed volume between the dressing and the tissue;

a housing defining an inner chamber, and including a reactor located in the inner chamber, the reactor being configured to chemically react with oxygen in the inner chamber;

a fluid passage connecting the inner chamber and the enclosed volume allowing for a flow of oxygen between the inner chamber and the enclosed volume; and a hose, wherein the system is configured to allow a user of the system to select a predetermined level of oxygen to be attained in the enclosed volume by the user:

selecting a desired length of the fluid passage among a plurality of different lengths prior to the reactor being exposed to oxygen in the inner chamber, wherein the desired length corresponds to the predetermined level of oxygen to be attained in the enclosed volume, and selecting the desired length of the fluid passage includes modifying the hose from an original length to a modified length.

3. The system according to claim 2, wherein the hose includes markings along a length of the hose indicating predetermined amounts of oxygen to be attained in the enclosed volume.

4. A system for controlling an amount oxygen in an enclosed volume, the system comprising:
   a dressing configured to seal to tissue so as to define the enclosed volume between the dressing and the tissue;

a housing defining an inner chamber, and including a reactor located in the inner chamber, the reactor being configured to chemically react with oxygen in the inner chamber;

a fluid passage connecting the inner chamber and the enclosed volume allowing for a flow of oxygen between the inner chamber and the enclosed volume; and a plurality of hoses having different cross-sectional areas;

wherein the system is configured to allow a user of the system to select a predetermined level of oxygen to be attained in the enclosed volume by the user;

selecting a desired cross-sectional area of the fluid passage among a plurality of different cross-sectional areas, wherein the desired cross-sectional area corresponds to the predetermined level of oxygen to be attained in the enclosed volume, and selecting the desired cross-sectional area of the fluid passage includes selecting one hose from the plurality of hoses having the desired cross-sectional area and connecting the one hose to the housing and to the dressing to at least partially define the fluid passage.

5. The system according to claim 4, wherein the system includes a plurality of adapters, each of the plurality of adapters being configured to connect one of the plurality of hoses to the housing and to the dressing.

6. The system according to claim 1, wherein:

the system includes a hose connected to the housing and to the dressing to at least partially define the fluid passage;

the system includes a clamp; and selecting the desired cross-sectional area of the fluid passage includes clamping the hose with the clamp so as to modify a cross-sectional area of the hose.

7. A system for controlling an amount oxygen in an enclosed volume, the system comprising:

a dressing configured to seal to tissue so as to define the enclosed volume between the dressing and the tissue;

a housing defining an inner chamber, and including a reactor located in the inner chamber, the reactor being configured to chemically react with oxygen in the inner chamber;

a fluid passage connecting the inner chamber and the enclosed volume allowing for a flow of oxygen between the inner chamber and the enclosed volume; and a hose connected to the housing and to the dressing to at least partially define the fluid passage, wherein the system is configured to allow a user of the system to select a predetermined level of oxygen to be attained in the enclosed volume by the user:

selecting a desired cross-sectional area of the fluid passage among a plurality of different cross-sectional areas, wherein the desired cross-sectional area corresponds to the predetermined level of oxygen to be attained in the enclosed volume, and selecting the desired cross-sectional area of the fluid passage includes arranging a porous solid in the hose.

8. The system according to claim 1, wherein:

the system includes a cover layer for selectively covering a desired portion of the dressing to reduce an oxygen permeability of the dressing.

9. The system according to claim 8, wherein:

the cover layer includes a metalized polymer film; and the cover layer is configured to be modified from an original size to a modified size that is less than the original size.

10. The system according to claim 1, wherein:

the housing includes a hose fitting and the dressing includes a dressing fitting; and the hose fitting is configured for attaching a hose to the housing and the dressing fitting is configured for attaching the hose to the dressing such that the hose at least partially defines the fluid passage.

11. The system according to claim 10, wherein the hose fitting and the dressing fitting are each a barbed fitting.

12. The system according to claim 2, wherein:

the system includes a cover layer for selectively covering a desired portion of the dressing to reduce an oxygen permeability of the dressing.

13. The system according to claim 4, wherein:

the system includes a cover layer for selectively covering a desired portion of the dressing to reduce an oxygen permeability of the dressing.

14. The system according to claim 7, wherein:

the system includes a cover layer for selectively covering a desired portion of the dressing to reduce an oxygen permeability of the dressing.

* * * * *